US008129444B2

(12) United States Patent
Hecht et al.

(10) Patent No.: US 8,129,444 B2
(45) Date of Patent: Mar. 6, 2012

(54) SELF-ADHESIVE DENTAL MATERIALS

(75) Inventors: Reinhold Hecht, Kaufering (DE);
Manfred Ludsteck, Geretsried (DE);
Thomas Luchterhandt, Greifenberg (DE); Markus Mikulla, Andechs-Frieding (DE)

(73) Assignee: 3M ESPE AG, Seefeld (DE)

( * ) Notice: Subject to any disclaimer, the term of this patent is extended or adjusted under 35 U.S.C. 154(b) by 1642 days.

(21) Appl. No.: 11/220,004

(22) Filed: Sep. 6, 2005

(65) Prior Publication Data
US 2006/0004122 A1   Jan. 5, 2006

Related U.S. Application Data

(63) Continuation of application No. 10/477,799, filed as application No. PCT/EP02/05218 on May 13, 2002, now abandoned.

(30) Foreign Application Priority Data

May 16, 2001  (DE) .................................. 101 24 028

(51) Int. Cl.
A61K 6/083 (2006.01)
A61K 6/08 (2006.01)
A61L 24/06 (2006.01)
A61C 5/04 (2006.01)
A61C 5/00 (2006.01)

(52) U.S. Cl. ........ 523/115; 523/113; 523/116; 523/118; 433/226; 433/228.1; 106/35

(58) Field of Classification Search .................. 523/113, 523/115, 116, 117, 118; 433/226, 228.1; 106/35
See application file for complete search history.

(56) References Cited

U.S. PATENT DOCUMENTS

| 3,066,112 A | 11/1962 | Bowen |
| 3,347,954 A | 10/1967 | Bredereck et al. |
| 3,541,068 A | 11/1970 | Taylor |
| 4,095,018 A | 6/1978 | Schmitt et al. |
| 4,278,738 A | 7/1981 | Brax et al. |
| 4,298,738 A | 11/1981 | Lechtken et al. |
| 4,443,587 A | 4/1984 | Schmitt et al. |
| 4,447,520 A | 5/1984 | Henne et al. |
| 4,522,693 A | 6/1985 | Henne et al. |
| 4,539,382 A | 9/1985 | Omura et al. |
| 4,544,742 A * | 10/1985 | Schmitt et al. ..................... 544/8 |
| 4,737,593 A | 4/1988 | Ellrich et al. |
| 4,820,744 A | 4/1989 | Kubota et al. |
| 4,872,936 A | 10/1989 | Engelbrecht |
| 5,043,361 A | 8/1991 | Kubota et al. |
| 5,063,257 A | 11/1991 | Akahane et al. |
| 5,154,762 A | 10/1992 | Mitra et al. |
| 5,171,763 A | 12/1992 | Ohno et al. |
| 5,244,933 A | 9/1993 | Eidenbenz et al. |
| 5,252,629 A | 10/1993 | Imai et al. |
| 5,367,002 A | 11/1994 | Huang et al. |
| 5,670,559 A * | 9/1997 | Zeng et al. ..................... 523/118 |
| 5,700,875 A | 12/1997 | Zeng et al. |
| 5,824,720 A | 10/1998 | Nowak et al. |
| 5,834,532 A | 11/1998 | Yamamoto et al. |
| 5,859,089 A | 1/1999 | Qian |
| 5,883,153 A * | 3/1999 | Roberts et al. ................. 523/116 |
| 5,925,690 A | 7/1999 | Fuchigami et al. |
| 5,968,998 A | 10/1999 | Jochum et al. |
| 6,048,913 A * | 4/2000 | Yamagishi et al. ............. 523/118 |
| 6,051,626 A | 4/2000 | Zeng et al. |
| 6,080,811 A | 6/2000 | Schehlmann et al. |
| 6,126,922 A | 10/2000 | Rozzi et al. |
| 6,127,451 A | 10/2000 | Qian |
| 6,217,644 B1 | 4/2001 | Matsunae et al. |
| 6,835,271 B1 | 12/2004 | Luchterhandt et al. |
| 6,852,775 B1 * | 2/2005 | Soglowek et al. ............. 523/109 |
| 2002/0061938 A1 * | 5/2002 | Hino .............................. 523/115 |
| 2002/0103272 A1 * | 8/2002 | Klee et al. ..................... 523/120 |
| 2002/0198284 A1 * | 12/2002 | Nakatsuka et al. ............ 523/116 |
| 2003/0083398 A1 * | 5/2003 | Kawashima et al. .......... 523/115 |

(Continued)

FOREIGN PATENT DOCUMENTS

DE         14 955 20         4/1969

(Continued)

OTHER PUBLICATIONS

Brock et al., "*Coatings Compendien Lehrbuch der Lacktechnologie Herausgegeben von Ulrich Zorll*," Vincentz, Hanover, Title pages, Publication page, and Table of Contents (8 pgs total) (1998). (Translation in English, "*Coatings Compendia Handbook of Paint Technology*," Title page and Table of Contents (9 pgs total)).

Fouassier, *Photoinitiation, Photopolymerization and Photocuring Fundamentals and Applications*, Hanser/Gardner Publications, Inc., Cincinnati, U.S., Title page, Publication page, and Table of Contents (7 pgs total) (1995).

Fouassier et al., Eds., *Radiation Curing in Polymer Science and Technology, vol. II Photoinitiating Systems*, Elsevier Applied Science, Essex, England, Title page, Publication page, and Table of Contents (4 pgs total) (1993).

(Continued)

*Primary Examiner* — Michael Pepitone
(74) *Attorney, Agent, or Firm* — Pamela L. Stewart

(57) ABSTRACT

The invention relates to a composition which is self-adhesive to the hard tooth tissue, comprising: (A) 5 to 75 percent by weight of one or more mono or higher functional ethylenically unsaturated compounds which additionally have an acid functional group, wherein one of said compounds has a P—OH group, for instance a phosphoric, phosphonic or phosphinic acid group; (B) 2 to 50 percent by weight of one or more mono or higher functional ethylenically unsaturated compounds without any acid functional group; (C) 22.8 to 85 percent by weight of filling material(s), comprising at least one filling material that may react with component (A) in the sense of causing a ion exchange, neutralization, salt formation and/or chelate formation reaction; (D) 0.1 to 8 percent by weight of one or more initiators and optionally activators; (E) 0.1 to 20 percent by weight of further additives, for example, modifiers, wherein the weight ration in % of component (A) relative to component (B) ranges from 21 to 90: 10 to 79.

43 Claims, No Drawings

U.S. PATENT DOCUMENTS

| | | | |
|---|---|---|---|
| 2003/0134932 A1* | 7/2003 | Lehmann et al. | 523/113 |
| 2003/0134934 A1* | 7/2003 | Kojima et al. | 523/120 |
| 2003/0158288 A1* | 8/2003 | Lehmann et al. | 523/115 |
| 2004/0002036 A1* | 1/2004 | Craig et al. | 433/215 |
| 2004/0097613 A1* | 5/2004 | Hecht et al. | 523/113 |
| 2004/0110864 A1 | 6/2004 | Hecht et al. | |
| 2004/0235981 A1 | 11/2004 | Qian | |
| 2005/0175966 A1* | 8/2005 | Falsafi et al. | 433/215 |

FOREIGN PATENT DOCUMENTS

| | | |
|---|---|---|
| DE | 20 61 513 | 6/1971 |
| DE | 26 58 538 A1 | 6/1977 |
| DE | 28 16 823 A1 | 10/1978 |
| DE | 35 36 076 A1 | 4/1987 |
| DE | 37 09 881 A1 | 10/1987 |
| DE | 39 41 629 A1 | 6/1990 |
| DE | 41 41 174 A1 | 6/1992 |
| DE | 199 42 923 A1 | 3/2000 |
| DE | 695 11 822 T2 | 5/2000 |
| DE | 198 82 513 T1 | 7/2000 |
| DE | 19 941 738 A1 | 3/2001 |
| DE | 695 18 037 T2 | 3/2001 |
| EP | 0 007 508 A2 | 6/1980 |
| EP | 0 047 902 A2 | 3/1982 |
| EP | 0 057 474 A2 | 8/1982 |
| EP | 0 073 413 A2 | 8/1982 |
| EP | 0 059 451 A1 | 9/1982 |
| EP | 0 007 508 B1 | 6/1983 |
| EP | 0 057 474 B1 | 10/1984 |
| EP | 0 047 902 B1 | 11/1984 |
| EP | 0 073 413 B1 | 12/1984 |
| EP | 0 059 451 B1 | 7/1985 |
| EP | 0 184 095 A2 | 6/1986 |
| EP | 0 219 058 A2 | 4/1987 |
| EP | 0 237 233 A2 | 9/1987 |
| EP | 0 184 095 B1 | 7/1989 |
| EP | 0 219 058 B1 | 6/1991 |
| EP | 0 480 472 A2 | 4/1992 |
| EP | 0 480 472 A3 | 4/1992 |
| EP | 0 588 878 B1 | 3/1994 |
| EP | 0 684 033 A1 | 11/1995 |
| EP | 0 480 472 B1 | 2/1996 |
| EP | 0 712 622 A1 | 5/1996 |
| EP | 0 717 977 A2 | 6/1996 |
| EP | 0 717 977 A3 | 6/1996 |
| EP | 0 738 928 A2 | 10/1996 |
| EP | 0 712 622 B1 | 9/1999 |
| EP | 0 684 033 B1 | 7/2000 |
| EP | 0 738 928 B1 | 6/2001 |
| GB | 1 316 129 | 5/1973 |
| GB | 1 576 080 | 10/1980 |
| JP | 05-255035 A | 10/1993 |
| JP | 2001-122718 A | 5/2001 |
| WO | WO 92/21314 A1 | 12/1992 |
| WO | WO 93/12759 A1 | 7/1993 |
| WO | WO 95/22956 A1 | 8/1995 |
| WO | WO 98/46198 A1 | 10/1998 |
| WO | WO 01/10389 A1 | 2/2001 |
| WO | WO 01/38449 A1 | 5/2001 |
| WO | WO 01/76536 A1 | 10/2001 |
| WO | WO 02092023 A1 * | 11/2002 |

OTHER PUBLICATIONS

Geurtsen et al., *Klinik der Kompositfullung*, Hanser/Gardner Publications, Inc., Cincinnati, U.S., Title page, Publication page, and Table of Contents (4 pgs. total) (1989). (Translation in English "Clinic of Composite Fillings," (3 pgs total)).

Hecht, "6. Basler Werkstoffkunde Symposium," (English translation: "6$^{th}$ Materials Science Symposium of Basel"), 25 pgs. (English translation is 9 pgs.) (Dec. 5-6, 2003).

Hecht et al., "RelyX Unicem First self-adhesive universal resin cement Scientific and Chemical Background Information," Austin, Texas, 67 pgs. (Mar. 2003).

Hecht et al., "Self-adhesion From a One Step to a "Zero Step" Bond Vision or Reality," Presentation at the Norwegian Dental Association, Oslo, Norway, 23 pgs. (Oct. 9, 2003).

Nanetti et al., *Coatings Compendien Lackrohstoffkunde*, Vincentz, Hanover, Title page, Publication page, and Table of Contents (7 pgs) (1997). (Translation in English, "Coatings Compendia Science of Paint Resins," (6 pgs total)).

D.C. Smith, "Development of glass-ionomer cement systems," *Biomaterials 19*, Title page, Publication page, Table of Contents, and pp. 467-478 (1998).

Staudinger et al., *Macromolecular Chemistry Book*, Basel, Switzerland 1966; Title page, table of contents and a section of chapter 1, 24 pages.

Webster, Ed., *vol. II, Prepolymers & Reactive Diluents Chemistry & Technology of UV & EB Formulation for Coatings, Inks & Paints*, John Wiley and Sons, London, UK, Title pages, Publication page, and Table of Contents (7 pgs total) (1996).

International Standard, ISO 4049, "Dentistry—Polymer-based filling, restorative and luting materials," Title page, Publication page, Table of Contents, Forward page, Introduction page, and pp. 1-27 (34 pp. total) (Jul. 15, 2000).

Material Safety Data Sheet, "Maxcem Paste Products, Indirect Cement, Base and Catalyst Paste," Kerr Corporation, Orange, California, 1 pg (Sep. 8, 2004).

Product Brochure: "Maxcem Self-Etch/Self-Adhesive Resin Cement" Retrieved from the Internet:<http://www.kerrhawe.com/products/documents/MXC_iu.pdf>; 2 pgs total; Feb. 22, 2005 [retrieved on Oct. 15, 2006].

Product Brochure: "Kerr Maxcem Frequently Asked Questions" Kerr Dentistry (a Subsidiary of Sybron Dental Specialties, Inc), Nov. 1, 2004; 3 pgs total.

* cited by examiner

SELF-ADHESIVE DENTAL MATERIALS

The present application is a continuation application of U.S. patent application Ser. No. 10/477,799, filed on 14 Nov. 2003 (pending), which is a U.S. National Stage Application of International Application Serial No. PCT/EP02/05218, filed 13 May 2002, which claims priority under 35 U.S.C. §119 of foreign application No. DE 101 24 028.7, filed 16 May 2001, which are all incorporated herein by reference.

The present invention relates to self-adhesive dental materials featuring a high level of adhesion to hard tooth substances, simplicity in use, and good mechanical properties. The compositions of the invention can be used in the dental segment as fillings, cements, core buildups, fissure sealants and as dental engineering materials.

In accordance with the present-day state of the art essentially the following classes of substance are used for the abovementioned end applications:
- amalgams
- glass ionomer cements (GICs)
- composites
- compomers
- resin-modified glass ionomer cements (RMGICs)

It is known that amalgams exhibit no self-adhesion to the hard tooth substances enamel and dentine. Amalgams are fixed solely by mechanical means, by way of what is known as an undercut preparation. Consequently there is a marginal gap between hard tooth substance and the amalgam, which is frequently the cause of unwanted development of secondary caries. These circumstances are described in detail, for example, in WO 93/12759.

In contrast to amalgam, the glass ionomer cements (GICs) exhibit weak adhesion to the hard tooth substances. The adhesion levels, however, are in the very low region of 1 MPa and are generally achieved only by a conditioning step beforehand. A further disadvantage of the GICs are the low mechanical values, in particular the low flexural strengths, which limit use in the area exposed to masticatory pressure.

Composites feature very good mechanical properties and excellent esthetics. In the cured form, composites are composed essentially of a crosslinked polymeric resin matrix based on (meth)acrylate monomers and a fraction of fillers. In order to protect the bond between resin matrix and filler against hydrolytic decomposition, composites are generally given an apolar, hydrophobic formulation. A consequence of this is that composites do not exhibit self-adhesion to the hard tooth substances and in particular not to dentine. Additionally, composites exhibit shrinkage in the course of curing, which allows marginal gaps to form and secondary caries to develop. In order to fix the composites adhesively to the hard tooth substances and to avoid the marginal gap, additional pretreatments and/or worksteps involving what is known as bonding are required. In accordance with the present state of the art it is necessary in this case for the practitioner to carry out the following worksteps:
- incipient etching of the entire hard tooth substances by means of a suitable acid such as phosphoric acid (total etch technique);
- application of a primer which penetrates the hard tooth substance superficially;
- application of a bonding material which together with the primer forms a hybrid layer;
- polymerization of the bonding material, for example, by irradiation with light; and/or redox reaction;
- application of the actual composite.

In order to reduce the number of worksteps the following, individual new methods have been developed in the meantime:
- Combination of the primer and bonding material to form one component.
- Combination of the primer and etching agent to form one component, which is no longer rinsed off after application.
- Combining of the etching agent, primer, and bonding material to form one solution, which now need only be applied and cured.

The processing of composites, therefore, is time-consuming and, moreover, is labor-intensive as a result of its sensitivity to moisture during the curing operation (placement of rubber dam). The problems referred to are documented, for example, in W. Geurtsen, Klinik der Kompositfüllung, Carl Hanser Verlag, Munich, Vienna 1989.

Compomers are chemically related to the composites. They are given a more hydrophilic formulation, however, through the use of acid-functional (meth)acrylates in the monomer mixture. With use of these materials, in contrast to the composites, there is no longer any need for absolute dryness (no placement of rubber dam). Nevertheless, these materials as well require the use of a bonding material in order to achieve an effective adhesive bond with the hard tooth substances.

The RMGICs are composed essentially of a basic filler, acids, water, (meth)acrylate-based monomers, and initiators for a free-radical polymerization. The RMGICs cure both by way of an acid/base reaction and by way of a free-radical polymerization. The esthetics of the RMGICs are improved as compared with those of the conventional GICs. Here again a conditioning step is generally necessary for adhesion—albeit minimal—to the hard tooth substances. Furthermore, the formulations of the products on the market include hydroxyethyl methacrylate (HEMA), which functions as a solubilizer for the water-soluble acids and remaining (meth)acrylates. HEMA is toxicologically objectionable and adversely affects the swelling characteristics and hence the mechanical properties, such as the flexural strength, of the RMGICs.

One object of the present invention can therefore be seen as being to provide dental materials which do not have the described disadvantages of the state of the art and which in particular feature simple application, a high level of adhesion to hard tooth substances without pretreatment such as the use of a conditioner, bonding material, primer or etching agent, for example, and also good mechanical properties.

Surprisingly it has been found that the object of the invention can be achieved by means of formulations comprising the following components:
(A) from 5 to 75% by weight of one or more mono- or polyfunctional ethylenically unsaturated compounds which additionally possess at least one acid-functional group, at least one of the compounds containing at least one P—OH group, such as a phosphoric, phosphonic or phosphinic acid group, for example,
(B) from 2 to 50% by weight of one or more mono- or polyfunctional ethylenically unsaturated compounds without an acid-functional group,
(C) from 22.8 to 85% by weight of filler(s), including at least one filler capable of reacting with component (A) in an ion exchange, neutralization, acid-forming and/or chelate-forming reaction,
(D) from 0.1 to 8% by weight of one or more initiators and, if desired, activators, (E) from 0.1 to 20% by weight of additional additives and/or modifiers, the weight ratio in % of component (A) to component (B) being in the range from 21 to 90:10 to 79, preferably in the range from 25 to 90:10 to 75, more preferably from 30 to 90:10 to 70 and very preferably from 40 to 80:20 to 60.

It has been found that formulations with the above composition exhibit an adhesion to bovine dental enamel or dentine of at least 2.0 MPa, preferably of at least 2.5 MPa, more preferably at least 3.0 MPa, measured in accordance with the adhesion determination method indicated below, "Determination of adhesion", without the need for pretreatment of the hard tooth substance. The formulations of the invention, moreover, have good mechanical properties and are easy to handle.

The following properties are characteristic of the formulations of the invention:
adhesion of at least 2.0 MPa, preferably at least 2.5 MPa, more preferably at least 3.0 MPa
low water absorbency of <50 µg/mm$^3$, preferably <40 µg/mm$^3$, more preferably <30 µg/mm$^3$
flexural strength of >30 MPa, preferably >40 MPa The term "pretreatment" encompasses steps such as etching, priming, bonding, and conditioning, for example.

The terms "include", "contain" or "comprise" introduce a nonexclusive enumeration of features. Similarly, the term "one" is to be understood in the sense of "at least one".

At least one monomer of component (A) contains at least one P—OH group, such as a phosphoric, phosphonic or phosphinic acid group, for example. This monomer is present preferably in a concentration of at least about 5% by weight, more preferably at least about 10% by weight, based on constituents (A) to (E).

Based on the fraction within component (A), this monomer is present preferably in an amount of at least 30%, more preferably at least 50% by weight.

It has also been found that a formulation wherein the weight ratio (in %) of component (A) to component (B) is in the range from 21 to 90:10 to 79, preferably in the range from 25 to 90:10 to 75, more preferably from 30 to 90:10 to 70 and very preferably from 40 to 80:20 to 60 has particularly advantageous properties.

Component (A) comprises compounds which possess at least one ethylenically unsaturated group and also at least one acid-functional group. The polymerizable groups are acrylic, methacrylic, vinyl and/or styryl groups, with acrylic and methacrylic groups being particularly preferred.

Examples of suitable acid groups are carboxylic acid residues, acid residues of phosphorus (e.g., phosphoric, phosphonic, phosphinic acids), of sulfur (e.g., sulfuric, sulfonic, sulfinic acids) and of boron. A feature of the acid groups is that they are able to enter into ion exchange, neutralization, salt-forming and/or chelate-forming reactions with reactive inorganic fillers. It is also possible for the acid residues of component (A) to be present not completely in free form but also, in part, in derivatized form, for instance as a salt, acid halide, acid hydride or readily hydrolyzable esters.

Suitable components (A) and their preparation are described for example in DE 35 36 076 A1, EP 0 237 233 A, and WO 95/22956. By way of example mention may be made of the following: 4-(meth)acryloyl-oxyethyltrimellitic acid, butenetricarboxylic acid, bis-4,6- and/or bis-2,5-(meth)acryloyloxyethyl-trimellitic acid, phosphoric esters of hydroxyethyl (meth)acrylate (HEMA), glyceryl di(meth)acrylate and/or pentaerythrityl tri(meth)acrylate, chloro- and bromo-phosphoric esters of bisphenol A glycidyl (meth)acrylate.

The use of oligomers or polymeric derivatives of abovementioned compounds also leads to dental materials of the invention having good properties.

Particular preference is given to the reaction products of nucleophilic acrylates and methacrylates such as 2-hydroxyethyl methacrylate (HEMA) or glycerol methacrylate esters, for example, with reactive phosphonic or phosphinic or phosphoric acid derivatives such as $POCl_3$, $P_2O_5$ or $PCl_3$, for example.

More preferably the abovementioned ethylenically unsaturated acids and/or derivatives thereof have a molecular weight in the range from 70 to 5 000, preferably in the range from 90 to 2 500, more preferably in the range from 100 to 1 000 g/mol.

Compounds suitable as component (B) are those which possess at least one ethylenically unsaturated group. The polymerizable groups are acrylic, methacrylic, vinyl and/or styryl groups, with acrylic and methacrylic groups being particularly preferred.

Suitable mono- and polyfunctional (meth)acrylates and also further ethylenically unsaturated compounds are described for example in EP 0 480 472 A, DE 39 41 629 C2 and in G. Webster (Ed.), Chemistry & Technology of UV & EB Formulation for Coatings, Inks and Paints, Vol. II Prepolymers & Reactive Diluents, J. Wiley and Sons, Chichester, N.Y., Weinheim, Brisbane, Toronto, Singapore, 1997. The ethylenically unsaturated compounds can be used in solitary form or in mixtures in the formulations.

Examples of suitable monomers are the acrylic and methacrylic esters of mono-, di- or higher poly-functional alcohols. By way of example mention may be made of the following: methyl(meth)acrylate, butyl(meth)acrylate, 2-ethylhexyl(meth)acrylate, lauryl(meth)acrylate, 2-hydroxyethyl(meth)acrylate, 2-hydroxypropyl(meth)acrylate, glyceryl 1,3-di(meth)acrylate (GDMA), glyceryl 1,2-di(meth)acrylate, cyclohexyl(meth)acrylate, phenyl(meth) acrylate, isobornyl(meth)acrylate, ethylene glycol di(meth) acrylate, 1,4-butanediol di(meth)acrylate, triethylene glycol di(meth)acrylate (TEGDMA), 1,6-hexanediol di(meth)acrylate, 1,12-dodecanediol di(meth)acrylate; trimethylolpropane tri(meth)acrylate, pentaerythrityl tetra(meth)acrylate, and dipentaerythrityl hexa(meth)acrylate.

With advantage it is also possible to use bisphenol A di(meth)acrylate and also the ethoxylated and/or propoxylated di(meth)acrylates derived therefrom. Also suitable are the monomers described in U.S. Pat. No. 3,066,112 A based on bisphenol A and glycidyl(meth)acrylate, or their derivatives formed by addition reaction with isocyanates.

Also highly suitable are the diacrylic and dimethacrylic esters of bis(hydroxymethyl)tri-cyclo[5.2.1.0$^{2,6}$]decane specified in DE 28 168 23 C and the diacrylic and dimethacrylic esters of the compounds of bis(hydroxymethyl)tricyclo[5.2.1.0$^{2,6}$]decane extended with from 1 to 3 ethylene oxide and/or propylene oxide units.

Additionally urethane(meth)acrylates such as 7,7,9-trimethyl-4,13-dioxo-5,12-diazahexadecane-1,16-dioxydi(meth) acrylate (UDMA, Plex 6661) can be a constituent of component (B). The stated compounds and their derivatives preferably have a molecular weight in the range from 70 to 5 000, preferably in the range from 90 to 2 500, more preferably in the range from 100 to 1 000 g/mol.

As component (C) it is possible to use inorganic fillers such as glasses or ceramics and/or organic fillers. The fillers can be used in solitary form or in mixtures. Furthermore, in order to optimize the product properties, the fillers can be incorporated in different particle sizes into the formulas, i.e., the fillers can have a unimodal or polymodal distribution, bimodal for example.

At least one filler must be used which is able to react with component (A) in an ion exchange, neutralization, salt-forming and/or chelate-forming reaction (reactive filler). In addition it is possible to use those fillers which are inert toward the acid functions of component (A) (nonreactive fillers). Furthermore, reinforcing materials, such as fibers or fibrous compounds, can also be added.

Fillers capable of reacting with the acid groups of component (A) are used, for example, to produce polycarboxylate cements and glass-ionomer cements and are described, for example, in D. C. Smith, Biomaterials 19, 467-478 (1998), DE 20 61 513 A, and WO 95/22956.

Suitable in principle are finely divided metals such as finely divided zinc, metal compounds such as the oxides and/or hydroxides of calcium, magnesium, strontium, and zinc. Also suitable are basic glass powders having a high fraction of divalent and trivalent ions, and also silicates which release metal cations, such as phyllo-silicates, bentonites or calcium silicates, sodium aluminum silicates, and zeolites, including the molecular sieves, and also apatite. Likewise suitable as glasses reactive toward component (A) are the borate, phosphate, and fluoroaluminosilicate glasses specified in WO 93/12759. Particularly preferred reactive fillers are the fluoroaluminosilicate glasses and also hydroxides of the alkaline earth metals.

Suitable inert inorganic fillers are, for example, quartz, zirconium silicates, precipitated silicates (HDKH) and low-solubility metal salts such as barium sulfate or calcium fluoride. Further inert inorganic fillers are described in WO 95/22956. Particularly preferred inert inorganic fillers are quartz and zirconium silicates. Component (C) here does not include, in the sense of the invention, any pyrogenic silicas.

Examples of organic fillers include bead polymers and copolymers based on methyl methacrylate, which are available commercially under the designation "Plexidon" or "Plex" from the company Röhm. Also particularly suitable are the polyurethane-based organic fillers described in DE 19 941 738.

For better incorporation into the polymer matrix it can be of advantage to surface-treat or surface-coat the stated fillers and also, if appropriate, X-ray-opaque additives using methods known for the skilled person. An example that may be mentioned is surface treatment with a silane such as methacryloxypropyltrimethoxy-silane. The amount of coating agent used is normally between 0.05 and 10% by weight, preferably between 0.1 and 5% by weight, based on the filler.

By initiators in accordance with component (D) are meant initiator systems which effect the free-radical polymerization of the monomers, examples being photo-initiators and/or what are called redox initiatory systems and/or thermal initiators.

Suitable photoinitiators are described for example in J.-P. Fouassier, Photoinitiation, Photopolymerization and Photo-curing, Hanser Publishers, Munich, Vienna, N.Y. 1995 or else J. F. Rabek (ed.), Radiation Curing in Polymer Science and Technology, Vol. II, Elsevier Applied Science, London, N.Y., 1993 and also in the patent publications EP 0 073 413 A, EP 0 007 508 A, EP 0 047 902 A, EP 0 057 474 A, and EP 0 184 095 A. Examples that may be mentioned include benzoin alkyl ethers, benzil ketals, and acylphosphine oxides. Particularly suitable are aliphatic and aromatic 1,2-diketone compounds such as camphorquinone in combination with activators such as tertiary amines.

Examples of suitable redox initiator systems include organic compounds with an oxidative action, such as peroxide compounds, together with what are termed activators. Suitable organic peroxide compounds include, in particular, compounds such as lauroyl peroxide, benzoyl peroxide, and also p-chlorobenzoyl and p-methylbenzoyl peroxide.

Examples of suitable activators include tertiary aromatic amines, such as the N,N-bis(hydroxyalkyl)-3,5-xylidines known from U.S. Pat. No. 3,541,068 A and the N,N-bis-(hydroxyalkyl)-3,5-di-t-butylanilines known from DE 26 58 538 A, especially N,N-bis(β-oxybutyl)-3,5-di-t-butylaniline, and also N,N-bis(hydroxyalkyl)-3,4,5-trimethylaniline. Further highly suitable activators are compounds of sulfur in oxidation state +2 or +4 such as sodium benzenesulfinate or sodium para-toluene-sulfinate or the barbituric acids or barbituric acid derivatives described in DE 14 955 20 B and also the malonylsulfamides described in EP 0 059 451 A. Preferred malonylsulfamides are 2,6-dimethyl-4-iso-butylmalonylsulfamide, 2,6-diisobutyl-4-propylmalonyl-sulfamide, 2,6-dibutyl-4-propylmalonylsulfamide, 2,6-dimethyl-4-ethylmalonylsulfamide and 2,6-dioctyl-4-isobutylmalonylsulfamide.

For further acceleration of curing the polymerization can be conducted in the presence of heavy metal compounds based on, for example, Ce, Fe, Cu, Mn, Co, Sn or Zn, with copper compounds being particularly suitable. The heavy metal compounds are used preferably in the form of soluble organic compounds.

One particularly suitable redox system comprises the following components:

I. from 14.9 to 50% by weight, preferably from 20 to 45% by weight, of a barbituric acid or thiobarbituric acid or of a barbituric or thiobarbituric acid derivative,
II. from 30 to 75% by weight, preferably from 35 to 67.8% by weight, of a peroxodisulfate compound and/or peroxodiphosphate compound,
III. from 10 to 35% by weight, preferably from 12 to 30% by weight, of a sulfinic acid compound, and
IV. from 0.1 to 5% by weight, preferably from 0.2 to 4% by weight, of a copper compound.

Where the dental compositions of the invention are cured by photopolymerization it is possible to formulate one-component systems. Where the dental compositions of the invention comprise a redox initiator system, comprising for example organic peroxide and activator, then for reasons of storage stability peroxide and activator are present in spatially separate parts of the dental composition of the invention, which are not mixed with one another until immediately prior to application. These, in other words, are at least two-component formulations in the form, for example, of powder/liquid or paste/paste.

For reasons of storage stability the constituents of the initiator system of the invention may be micro-encapsulated. Methods of microencapsulation are described for example in U.S. Pat. No. 5 154 762 and EP 0 588 878 B1.

In order to set specific properties it is possible as component (E) to introduce additional additives or modifiers into the formulations. Possible additives and their functions are described in U. Zorll (ed.), Lehrbuch der Lacktechnologie, Vincentz Verlag, Hanover 1998 and P. Nanetti, Lackrohstoffkunde, Vincentz Verlag, Hanover 1997. With no claim to completeness, representative mention may be made of some additives and/or modifiers:

plasticizers such as phthalates, adipates, sebacates, phosphates or citrates, for example to increase the flexibility of the compositions;

organic and inorganic pigments and/or dyes such as white pigments based on titanium dioxide or zinc sulfide (lithopones), red iron oxide 3395, Bayferrox 920 Z Yellow, Neozapon Blue 807 (copper phthalocyanine-based dye) or Helio Fast Yellow ER, for individual coloring of the dental compositions;

stabilizers, especially free-radical scavengers, such as substituted and unsubstituted hydroxyaromatics (e.g., para-methoxyphenol), phenothiazine, HALS (hindered amine light stabilizers) and/or heavy metal scavengers such as EDTA;

thixotropic assistants such as pyrogenic silicas (Aerosil) or else modified phyllosilicates;

ion donor substances, particularly those which release fluoride ions, such as the fluoride salts of metals from main groups one and/or two such as sodium fluoride. Particularly suitable are complex inorganic fluorides of the general formula $A_nMF_m$ as described in EP 0 717977 A. In this formula A is a mono- or polyvalent cation, M is a metal from main or transition group III, IV, V, n is an integer from 1 to 3, and m is an integer from 3 to 6. As representatives mention may be made of calcium zinc fluoride and potassium hexafluorotitanate.

Bactericidal or antibiotic substances such as chlorhexidine, pyridinium salts or the customary pharmaceutical substances such as β-lactam antibiotics (penicillins), cephalosporins, tetracyclines, chloramphenicol, fosfomycin, antibacterial macrolides or polypeptide antibiotics, for example, may likewise be used.

It is also possible to use solvents as flow improvers and to improve the mixing characteristics. Particularly preferred in this context are water, acetone, methyl ethyl ketone and/or short-chain alcohols having less than 10 carbon atoms such as ethanol or isopropanol, for example.

Furthermore, in order to set specific properties, it is also possible as component (E) to use soluble organic polymers such as polyvinyl acetate, polyacrylic acid and/or polyvinyl ethers.

The compositions of the invention can be used in the dental segment, for example, as filling materials, fissure sealants, cements, core buildups and as dental engineering materials and/or bone substitute compositions.

The invention is described in more detail below with reference to examples, which should not be understood as limiting the invention in any way whatsoever.

EXPERIMENTAL SECTION

Example 1

Light-curing Filling Material as 2 K [2-Component] System (Powder/Liquid), Comprising 3.8 Parts Powder and 1 Part Liquid Powder:
(C) 98% by weight of strontium aluminum fluorosilicate glass, silanized with 0.075% by weight of methacryloxypropyltrimethoxysilane
(E) 1% by weight of. pyrogenic silica (Aerosil OX 50), silanized with 3% by weight of methacryloxypropyltrimethoxysilane
(C) 1% by weight of calcium hydroxide
Liquid:
(A) 49.44% by weight of hydroxyethyl methacrylate phosphate
(B) 30% by weight of propoxylated bisphenol A dimethacrylate
(B) 20% by weight of triethylene glycol dimethacrylate (TEGDMA)
(D) 0.26% by weight of dimethylaminoethyl benzoate
(D) 0.2% by weight of camphorquinone
(D) 0.1% by weight of Cu(II) acetate Example 2

Light-curing Filling Material as 2 K [2-Component] System (Powder/Liquid), Comprising 3.8 Parts Powder and 1 Part Liquid Powder:
(C) 93.5% by weight of strontium aluminum fluorosilicate glass, silanized with 0.075% by weight of methacryloxypropyltrimethoxysilane
(C) 1% by weight of calcium hydroxide
(D) 0.5% by weight of dimethylaminoethyl benzoate
(E) 5.0% by weight of pyrogenic silica (Aerosil OX 50), silanized with 3% by weight of methacryloxy-propyltrimethoxysilane
Liquid:
(A) 69.7% by weight of 1,3-glyceryl dimethacrylate phosphate
(B) 30% by weight of TEGDMA
(D) 0.2% by weight of camphorquinone
(D) 0.1% by weight of Cu(II) ethylhexanate Example 3

Light-Curing Filling Material as 1K [1-Component] Paste

A laboratory kneader was used to produce a paste from the following constituents:
(C) 74% by weight of strontium aluminum fluorosilicate glass, silanized with 0.3% by weight of methacryloxypropyltrimethoxysilane
(E) 5% by weight of pyrogenic silica (Aerosil OX 50), silanized with 3% by weight of methacryloxypropyltrimethoxysilane
(C) 1% by weight of calcium hydroxide
(D) 0.4% by weight of dimethylaminoethyl benzoate
(A) 13.46% by weight of 1,3-glyceryl dimethacrylate phosphate
(B) 6% by weight of TEGDMA
(D) 0.04% by weight of camphorquinone
(D) 0.1% by weight of Cu(II) acetate Example 4

Dual-curing Fixing Cement as 2 K [2-Component]System (Powder/Liquid), Comprising 3 Parts Powder and 1 Part Liquid Powder:
(C) 88.6% by weight of strontium aluminum fluorosilicate glass, silanized with 0.3% by weight of methacryloxypropyltrimethoxysilane
(C) 1.6% by weight of calcium hydroxide
(D) 0.8% by weight of sodium toluenesulfinate
(D) 1.2% by weight of 1,3-dimethyl-5-phenylbarbituric acid
(D) 2.4% by weight of sodium peroxodisulfate
(E) 5.4% by weight of pyrogenic silica (Aerosil OX 50), silanized with 3% by weight of methacryloxy-propyltrimethoxysilane Liquid:

(A) 49.5% by weight of 1,3-glyceryl dimethacrylate phosphate (B) 20% by weight of propoxylated bisphenol A dimethacrylate (B) 30% by weight of triethylene glycol dimethacrylate (D) 0.2% by weight of camphorquinone (D) 0.1% by weight of Cu(II) acetate (E) 0.2% by weight of 2,6-di-tert-butyl-4-methylphenol Comparative Examples (See Table 1)

Commercially available filling materials from different classes of material

Ketac Molar (GIC from 3M ESPE AG)

Fuji II LC (RMGIC from GC)

Dyract AP (Compomer from Dentsply)

Tetric Ceram (Composite from Vivadent)

Comparative Examples (See Table 2)

Commercially available fixing cements from different classes of material

Ketac Cem (GIC from 3M ESPE AG)

Fuji Plus (RMGIC from GC)

Dyract Cem Plus (Compomer from Dentsply)

Panavia 21 (Composite from Kuraray)

Description of Measurements Conducted

Determination of Adhesion:

Adhesion tests were carried out using bovine teeth. For each test, five bovine teeth deep frozen following extraction are thawed, cleaned to remove the remaining gum, and separated from the roots by sawing with a diamond saw. The remaining pulp is removed with the aid of a pulp needle and the teeth are then rinsed with mains water. Planar dentine is obtained by labial sanding of the teeth on a water-cooled diamond sanding disk. The teeth are then embedded in silicone in such a way that the sanded-off surface, which is kept well moistened, points upward, and are subsequently after-treated wet with a fine silicon carbide sandpaper. Then each tooth has stuck to it a small wax plate which has a round cutout of 6 mm in diameter (test area). This test area is filled in a planar fashion with the material, mixed according to the manufacturer's instructions, and cured in accordance with the manufacturer's instructions for 10 to 40 seconds with Elipar II (600-800 mW/cm$^2$). Autopolymerizing materials are cured for 1 h at 36° C. and 100% relative humidity. After curing, the small wax plate is removed, a screw is bonded adhesively to the protruding filling at right angles to the surface of the tooth, and after storage for one day at 36° C. and 100% relative humidity the adhesion is measured in a take-off test on a Zwick UPM 1455 with a take-off rate of 1 mm/min.

The flexural strength was determined in accordance with EN ISO 4049: 2000 (3-point bending test). The water absorption was determined on standardized test specimens in accordance with EN ISO 4049: 2000.

The results of the flexural strength and adhesion measurements and also of the water absorption are compiled in tables 1 and 2 (lc=light-cured, dc=dark-cured).

TABLE 1

| Material | Flexural strength [MPa] | Adhesion to dentine [MPa] | Water absorption [µg/mm$^3$] |
| --- | --- | --- | --- |
| Ketac Molar (GIC), dc | 40 | 0.0 | 61 |
| Fuji II LC (RMGIC), lc | 43 | 0.4 | 129 |
| Dyract AP (Compomer), lc | 100 | 0.0 | 18 |
| Tetric Ceram (Composite), lc | 108 | 0.0 | 13 |
| Example 1, lc | 70 | 3.4 | 20 |
| Example 2, lc | 72 | 3.7 | 23 |
| Example 3, lc | 75 | 3.3 | 19 |

The example formulas 1 to 3 of the invention exhibit without pretreatment a much higher adhesion to bovine dentine than all other materials. In comparison with the glass ionomer cements and resin-modified glass ionomer cements, moreover, the flexural strengths are greatly increased. The water absorptions are within the range of the compomers and composites and are much lower than in the case of the glass ionomer cements and resin-modified glass ionomer cements.

TABLE 2

| Material | Flexural strength [MPa] | Adhesion to dentine [MPa] | Water absorption [µg/mm$^3$] |
| --- | --- | --- | --- |
| Ketac Cem (GIC), dc | 17 | 0 | 60 |
| Fuji Plus (RMGIC), dc | 18 | 0.9 | 171 |
| Dyract Gem Plus (Compomer), dc | 58 | 0 | 51 |
| Panavia 21 (Composite), dc | 94 | 0 | 28 |
| Example 4 dc | 61 | 4.1 | 25 |
| lc | 66 | 5.7 | 24 |

The example formula 4 of the invention exhibits without pretreatment a very high adhesion to bovine dentine. The water absorptions are within the range of the composites and are much lower than in the case of the compomers, glass ionomer cements, and resin-modified glass ionomer cements.

Example 5

Light-curing Fissure Sealing Material as 1K [1-Component] Paste

A laboratory kneader was used to produce a paste from the following constituents:

(A) 21% by weight of di-HEMA phosphate (A) 5% by weight of trimellitic acid di-HEMA ester (A) 10% by weight of 1,3-glyceryldimethacrylate phosphate (B) 5% by weight of bis-GMA (C) 55% by weight of quartz silanized with 3% by weight of methacryloxypropyltrimethoxysilane (C) 1% by weight of calcium hydroxide (D) 0.9% by weight of dimethylaminoethyl benzoate (D) 1.1% by weight of camphorquinone (E) 1% by weight of pyrogenic silica (Aerosil OX 50) silanized with 3% by weight of methacryloxypropyltrimethoxysilane

| Material | Flexural strength [MPa] | Adhesion to dentine [MPa] | Water absorption [µg/mm$^3$] |
| --- | --- | --- | --- |
| Example 5, 1c | 50 | 3.1 | 19 |

The invention claimed is:

1. A self-adhesive dental material comprising:
   (A) from 5 to 75% by weight of one or more mono- or polyfunctional ethylenically unsaturated compounds which additionally possess at least one acid-functional group, at least one of the compounds containing at least one P—OH group,
   (B) from 2 to 50% by weight of one or more mono- or polyfunctional ethylenically unsaturated compounds without an acid-functional group,
   (C) from 22.8 to 85% by weight of filler(s), including at least one filler capable of reacting with component (A) in an ion exchange, neutralization, acid-forming and/or chelate-forming reaction,
   (D) from 0.1 to 8% by weight of one or more initiators and, if desired, activators,
   (E) from 0.1 to 20% by weight of additional additives and/or modifiers,
   the weight ratio in % of component (A) to component (B) being in the range from 21 to 90:10 to 79, and with the proviso that the self-adhesive dental composition does not comprise added water.

2. The self-adhesive dental material of claim 1, wherein the monomer in component (A) having at least one P—OH group is present in a concentration of at least 5% by weight based on the constituents (A) to (E).

3. The self-adhesive dental material of claim 1, wherein the polymerizable groups of component (A) comprise acrylic, methacrylic, vinyl and/or styryl groups and the acid groups are selected from the group consisting of carboxylic acid residues, acid residues of phosphorus, sulfur, boron, and combinations thereof.

4. The self-adhesive dental material of claim 1, wherein the polymerizable groups of component (B) comprise acrylic, methacrylic, vinyl and/or styryl groups.

5. The self-adhesive dental material of claim 1, wherein component (C) comprises fillers which are inert toward the acid functions of component (A).

6. The self-adhesive dental material of claim 1, wherein component (D) is selected from photoinitiators and/or redox initiator systems.

7. The self-adhesive dental material of claim 1, wherein component (E) is selected from the group consisting of plasticizers, organic pigments, inorganic pigments, dyes, stabilizers, heavy metal scavengers, thixotropic assistants, ion donor substances, bactericidal substances, and antibiotic substances.

8. The self-adhesive dental material of claim 1, wherein the self-adhesive dental material is a filling material, fissure sealant, cement or core buildup material.

9. A method of producing a self-adhesive dental material comprising a) preparing hard dental tissue, b) directly applying the self-adhesive dental material of claim 1 into the preparation, and c) curing the self-adhesive dental material, in which no pretreatment steps are carried out before step b).

10. The self-adhesive dental composition of claim 1 wherein component (C) is present in an amount of from 40 to 85% by weight.

11. The self-adhesive dental material of claim 1 wherein the dental material has a water absorbency of less than 50 µg/mm$^3$.

12. The self-adhesive dental material of claim 11 wherein the dental material has a water absorbency of less than 40 µg/mm$^3$.

13. The self-adhesive dental material of claim 12 wherein the dental material has a water absorbency of less than 30 µg/mm$^3$.

14. The self-adhesive dental material of claim 1 wherein the dental material has a flexural strength of greater than 30 MPa.

15. The self-adhesive dental material of claim 14 wherein the dental material has a flexural strength of greater than 40 MPa.

16. The self-adhesive dental material of claim 1 wherein the one or more mono- or polyfunctional ethylenically unsaturated compounds which additionally possess at least one acid-functional group are compounds selected from the group consisting of 4-(meth)acryloyl-oxyethyltrimellitic acid, butenetricarboxylic acid, bis-4,6-and/or bis-2,5-(meth)acryloyloxyethyltrimellitic acid, phosphoric esters of hydroxyethyl (meth)acryl ate (HEMA), glyceryl di(meth)acrylate and/or pentaerythrityl tri(meth)acrylate, chloro- and/or bromo-phosphoric esters of bisphenol A glycidyl (meth)acrylate.

17. The self-adhesive dental material of claim 1 wherein the one or more mono- or polyfunctional ethylenically unsaturated compounds which additionally possess at least one acid-functional group are oligomers and/or polymers of compounds selected from the group consisting of 4-(meth)acryloyl-oxyethyltrimellitic acid, butenetricarboxylic acid, bis-4, 6- and/or bis-2,5-(meth)acryloyloxyethyltrimellitic acid, phosphoric esters of hydroxyethyl (meth)acrylate (HEMA), glyceryl di(meth)acrylate and/or pentaerythrityl tri(meth) acrylate, chloro- and/or bromo-phosphoric esters of bisphenol A glycidyl (meth)acrylate.

18. The self-adhesive dental material of claim 1 wherein the one or more mono- or polyfunctional ethylenically unsaturated compounds without an acid-functional group are acrylic and/or methacrylic esters of mono-, di- and/or higher polyfunctional alcohols.

19. The self-adhesive dental material of claim 18 wherein the acrylic and/or methacrylic esters are selected from the group consisting of methyl (meth)acrylate, butyl (meth)acrylate, 2-ethylhexyl (meth)acrylate, lauryl (meth)acrylate, 2-hydroxyethyl (meth)acrylate, 2 hydroxypropyl (meth)acrylate, glyceryl 1,3-di(meth)acrylate (GDMA), glyceryl 1,2-di (meth)acrylate, cyclohexyl (meth)acrylate, phenyl (meth) acrylate, isobornyl (meth)acrylate, ethylene glycol di(meth) acrylate, 1,4-butanediol di(meth)acrylate, triethylene glycol di(meth)acrylate (TEGDMA), 1,6-hexanediol di(meth)acrylate, 1,12 dodecanediol di(meth)acrylate, trimethylolpropane tri(meth)acrylate, pentaerythrityl tetra(meth)acrylate, and dipentaerythrityl hexa(meth)acrylate.

20. The self-adhesive dental material of claim 1 wherein the one or more mono- or polyfunctional ethylenically unsaturated compounds without an acid-functional group are urethane (meth)acrylates.

21. The self-adhesive dental material of claim 20 wherein the urethane (meth)acrylate is 7,7,9 trimethyl-4,13-dioxo-5, 12-diazahexadecane-1,16-dioxydi(meth)acrylate.

22. The self-adhesive dental material of claim 20 wherein the urethane (meth)acrylate has a molecular weight in the range from 70 to 5000 g/mol.

23. The self-adhesive dental material of claim 22 wherein the urethane (meth)acrylate has a molecular weight in the range from 90 to 2500 g/mol.

24. The self-adhesive dental material of claim 23 wherein the urethane (meth)acrylate has a molecular weight in the range from 100 to 1000 g/mol.

25. The self-adhesive dental material of claim 1 wherein the one or more initiators are organic peroxide compounds selected from the group consisting of lauroyl peroxide, benzoyl peroxide, p-chlorobenzoyl peroxide, and p-methylbenzoyl peroxide.

26. The self-adhesive dental material of claim 1 wherein component (D) comprises an activator selected from the group consisting of N,N-bis(hydroxyalkyl) -3,5-xylidines, N,N-bis(hydroxyalkyl)-3,5-di-t-butylanilines, N,N-bis(hydroxyalkyl) -3,4,5-trimethylaniline, sodium benzenesulfinate, sodium para-toluenesulfinate, barbituric acids, and malonylsulfamides.

27. The self-adhesive dental material of claim 26 wherein the malonylsulfamides are selected from the group consisting of 2,6-dimethyl-4-isobutylmalonylsulfamide, 2,6-diisobutyl-4-propylmalonylsulfamide, 2,6-dibutyl-4-propylmalonylsulfamide, 2,6 dimethyl-4-ethylmalonylsulfamide, and 2,6-dioctyl-4-isobutylmalonylsulfamide.

28. The self-adhesive dental material of claim 1 further comprising a heavy metal compound.

29. The self-adhesive dental material of claim 28 wherein the heavy metal compound is a soluble organic compound.

30. The self-adhesive dental material of claim 28 wherein the heavy metal compound comprises a metal selected from the group consisting of Ce, Fe, Cu, Mn, Co, Sn, and Zn.

31. The self-adhesive dental material of claim 1 wherein the additional additives and/or modifiers comprise bactericidal or antibiotic substances.

32. The self-adhesive dental material of claim 31 wherein the bactericidal or antibiotic substances are selected from the group consisting of chlorhexidine, pyridinium salts, β-lactam antibiotics, cephalosporins, tetracyclines, chloramphenicol, fosfomycin, antibacterial macrolides, and polypeptide antibiotics.

33. The self-adhesive dental composition of claim 7 wherein the composition consists essentially of components (A), (B), (C), (D), and (E).

34. The self-adhesive dental composition of claim 33 wherein the composition consists of components (A), (B), (C), (D), and (E).

35. A self-adhesive dental material comprising:
(A) from 5 to 75% by weight of one or more mono- or polyfunctional ethylenically unsaturated compounds which additionally possess at least one acid-functional group, at least one of the compounds containing at least one P—OH group,
(B) from 2 to 50% by weight of one or more mono- or polyfunctional ethylenically unsaturated compounds without an acid-functional group,
(C) from 22.8 to 85% by weight of filler(s), including at least one filler capable of reacting with component (A) in an ion exchange, neutralization, acid-forming and/or chelate-forming reaction,
(D) from 0.1 to 8% by weight of one or more initiators and, if desired, activators,
wherein the one or more initiators comprise a redox initiator system comprising:
a barbituric acid, a thiobarbituric acid, or a combination thereof;
a peroxodisulfate compound, a peroxodiphosphate compound, or a combination thereof;
a sulfinic acid compound; and
a copper compound, and
(E) from 0.1 to 20% by weight of additional additives and/or modifiers,
the weight ratio in % of component (A) to component (B) being in the range from 21 to 90:10 to 79.

36. A self-adhesive dental material comprising:
(A) from 5 to 75% by weight of one or more mono- or polyfunctional ethylenically unsaturated compounds which additionally possess at least one acid-functional group, at least one of the compounds containing at least one P—OH group,
(B) from 2 to 50% by weight of one or more mono- or polyfunctional ethylenically unsaturated compounds without an acid-functional group,
(C) from 22.8 to 85% by weight of filler(s), including at least one basic glass powder having a high fraction of divalent and trivalent ions,
(D) from 0.1 to 8% by weight of one or more initiators and, if desired, activators, and
(E) from 0.1 to 20% by weight of additional additives and/or modifiers,
the weight ratio in % of component (A) to component (B) being in the range from 21 to 90:10 to 79, and
with the proviso that the self-adhesive dental composition does not comprise added water.

37. The self-adhesive dental material of claim 36 wherein the at least one basic glass powder having a high fraction of divalent and trivalent ions is selected from the group consisting of a borate glass, a phosphate glass, and a fluoroaluminosilicate glass.

38. The self-adhesive dental material of claim 37 wherein the at least one basic glass powder having a high fraction of divalent and trivalent ions is a fluoroaluminosilicate glass.

39. A method of treating a hard tooth substance, the method comprising:
mixing together components (A), (B), (C), (D), and (E) of a self-adhesive dental material according to claim 1;
applying the mixed self-adhesive dental material to the hard tooth substance; and
curing the applied self-adhesive dental material.

40. The method of claim 39 wherein applying comprises applying the mixed self-adhesive dental material to the hard tooth substance without pretreatment of the hard tooth substance.

41. The method of claim 40 wherein the cured self-adhesive dental material has an adhesion to the hard tooth substance of at least 2 MPa.

42. The method of claim 41 wherein the hard tooth substance comprises enamel.

43. The method of claim 41 wherein the hard tooth substance comprises dentine.

* * * * *

UNITED STATES PATENT AND TRADEMARK OFFICE
CERTIFICATE OF CORRECTION

PATENT NO. : 8,129,444 B2
APPLICATION NO. : 11/220004
DATED : March 6, 2012
INVENTOR(S) : Reinhold Hecht It is certified that error appears in the above-identified patent and that said Letters Patent is hereby corrected as shown below:

First Page, Column 2
(Other Publications)   Delete "Lackterchnologie" and insert -- Lacktechnologie --, therefor.

Column 2
Line 17   Delete "Kompositftullung," and insert -- Kompositfüllung, --, therefor.

Column 9
Lines 46-47 (Approx.)   Delete "aftertreated" and insert -- after treated --, therefor.

Column 12
Line 23   In Claim 16, delete "(meth)acryl ate" and insert -- (meth)acrylate --, therefor.
Line 46   In Claim 19, delete "2 hydroxypropyl" and insert -- 2-hydroxypropyl --, therefor.
Line 52   In Claim 19, delete "1,12 dodecanediol" and insert -- 1,12-dodecanediol --, therefor.

Signed and Sealed this
Fourteenth Day of August, 2012

David J. Kappos
*Director of the United States Patent and Trademark Office*